(12) United States Patent
Hugon

(10) Patent No.: US 6,568,659 B2  
(45) Date of Patent: May 27, 2003

(54) DEVICE FOR DIFFUSING AROMAS

(75) Inventor: Alain Hugon, Crozet (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/167,297

(22) Filed: Jun. 10, 2002

(65) Prior Publication Data

US 2002/0153622 A1 Oct. 24, 2002

Related U.S. Application Data

(63) Continuation of application No. PCT/IB00/01635, filed on Nov. 10, 2000.

(30) Foreign Application Priority Data

Dec. 17, 1999 (EP) ............................................. 99125212

(51) Int. Cl.$^7$ ................................................. B01F 3/04
(52) U.S. Cl. ................ 261/30; 261/107; 261/DIG. 88; 422/124
(58) Field of Search .......................... 261/30, 104, 107, 261/DIG. 65, DIG. 88, DIG. 89; 422/123, 124

(56) References Cited

U.S. PATENT DOCUMENTS

| 1,911,871 A | * | 5/1933 | Andersen ...................... 261/30 |
| 3,633,881 A | * | 1/1972 | Yurdin ......................... 239/44 |
| 5,565,148 A |   | 10/1996 | Pendergrass, Jr. ............. 261/30 |

FOREIGN PATENT DOCUMENTS

| FR | 2670568 | 6/1992 |
| WO | WO 9628195 A | 9/1996 |

* cited by examiner

*Primary Examiner*—Robert A. Hopkins  
(74) *Attorney, Agent, or Firm*—Winston & Strawn

(57) ABSTRACT

The invention relates to a device for diffusing aromas that includes a bottle containing the aromatic product to be diffused in a liquid state, the bottle being removably mounted beneath a device body. The body has an inner chamber which communicates with the bottle in the operating position and horizontal entrance/exit passages which are connected to a pressurized air circuit which opens into the chamber. A diffusion screen is arranged inside the inner chamber, perpendicularly to the axis of the horizontal passages, and a capillary element connects the liquid contained in the bottle to the diffusion screen.

15 Claims, 2 Drawing Sheets

DEVICE FOR DIFFUSING AROMAS

CROSS-REFERENCE TO RELATED APPLICATIONS

The present application is a continuation of the US national stage designation of International application PCT/IB00/01635 filed Nov. 10, 2000, the content of which is expressly incorporated herein by reference thereto.

TECHNICAL FIELD AND BACKGROUND ART

The present invention concerns a device for the diffusion of aroma, as well as an apparatus for the olfactive evaluation of scents comprising a plurality of such devices. By aroma, it is understood here any odor (scent, fragrance) diffused by a pure compound or by an odorant or perfumed composition in liquid form.

Several types of scent diffusers are already known, which can be used either by professionals to test a new pure fragrance or to carry out a new perfumed mixture, as well as by the public at large, for example for the choice of a perfume. Such known diffusors are based either on the formation of an odorant mist (nebulization) or on the carrying of a fragrance, by means of air or a neutral gas, from a porous carrier or from a polymer in which the odorant liquid is absorbed.

Now, both these two types of diffusors have disadvantages and do not therefore satisfy users. In the case of nebulization, the major disadvantage is in the presence, in the tested fluid, of micro-drops of the liquid aromatic product that can affect the evaluation by the user of its real odor. In the second type of diffusers, the porous mineral carrier or the polymer that is used as the storage means for the odorant liquid can provoke odor modifications and thus disturb the evaluation of the real odor of the tested liquid product.

Therefore, the aim of the present invention is to provide a device for the diffusion of scent which can be used in a similar manner to that of the known diffusers without however having their disadvantages, and this by avoiding both the nebulization of the odorant liquid product to be tested and the use of a porous carrier for the storage by absorption of the product.

SUMMARY OF THE INVENTION

The device for the diffusion of a scent or aroma comprises a bottle having a bottom and defining an interior that contains therein a liquid aromatic product that includes an aroma to be diffused. A device body is included for diffusing the aroma from the liquid aromatic product, with the body being removably mounted on the bottle and having an inner chamber which communicates with the bottle interior when in an operating position. The device advantageously includes entrance and exit channels for movement of air, with the channels being connected to a pressurized air circuit that opens into the inner chamber and causes movement of air along a path from the entrance to exit channels. A diffusion screen is arranged in the inner chamber and positioned in the moving air path and a capillary element extending from the liquid aromatic product to the diffusion screen is included for directing the liquid aromatic product to the diffusion screen under capillary action. This arrangement enables the screen to expose the liquid aromatic product to the moving air that carries the aroma out of the device. Preferably, the diffusion screen is mounted between the entrance and exit passages in a position that is perpendicular to the air movement path so that it can carry the aroma without also carrying microdrops of the liquid aromatic product.

The capillary element may be a hollow needle having one end that cooperates with the diffusion grid and another end disposed inside the bottle interior. Preferably, a wick is disposed inside the hollow needle, wherein one end of the wick is in contact with the diffusion screen and another end positioned close to the bottom of the bottle. Also, a cut-flow grid may be arranged in the inner chamber adjacent the diffusion screen to assist in the avoidance of microdrops being carried by the moving air stream. Advantageously, operating means for adjusting pressurized air flow and air movement through the passages are provided.

The invention also relates to an apparatus for dispensing and evaluating aroma odors, comprising a plurality of the devices described herein, and a main frame having a central portion around which the plurality of devices are mounted, wherein the exit channels of the devices are located in the central part of the frame. The apparatus can have either a circular or polygonal frame around which each exit passage is arranged to direct aroma containing air toward the central portion of the frame. In a preferred arrangement, the frame is octagonal.

If desired, a cover having a central aperture directed upwards and covering the exit channels can be provided. Also, operating means for adjusting pressurized air flow and air movement through the passages of each of the devices may be provided. When so provided, the means for operating the devices is assembled on a same panel and with a common source of pressurized air for all the devices. This enables each device to be operated individually or multiple devices to be operated simultaneously.

BRIEF DESCRIPTION OF THE DRAWINGS

The present invention will now be described in further detail by reference to the annexed drawing. The annexed drawings show, schematically and by way of example, an embodiment of the device for diffusion, respectively of the apparatus for odor evaluation of scent, according to the invention.

DETAILED DESCRIPTION OF THE PREFERRED EMBODIMENTS

Figure 1:
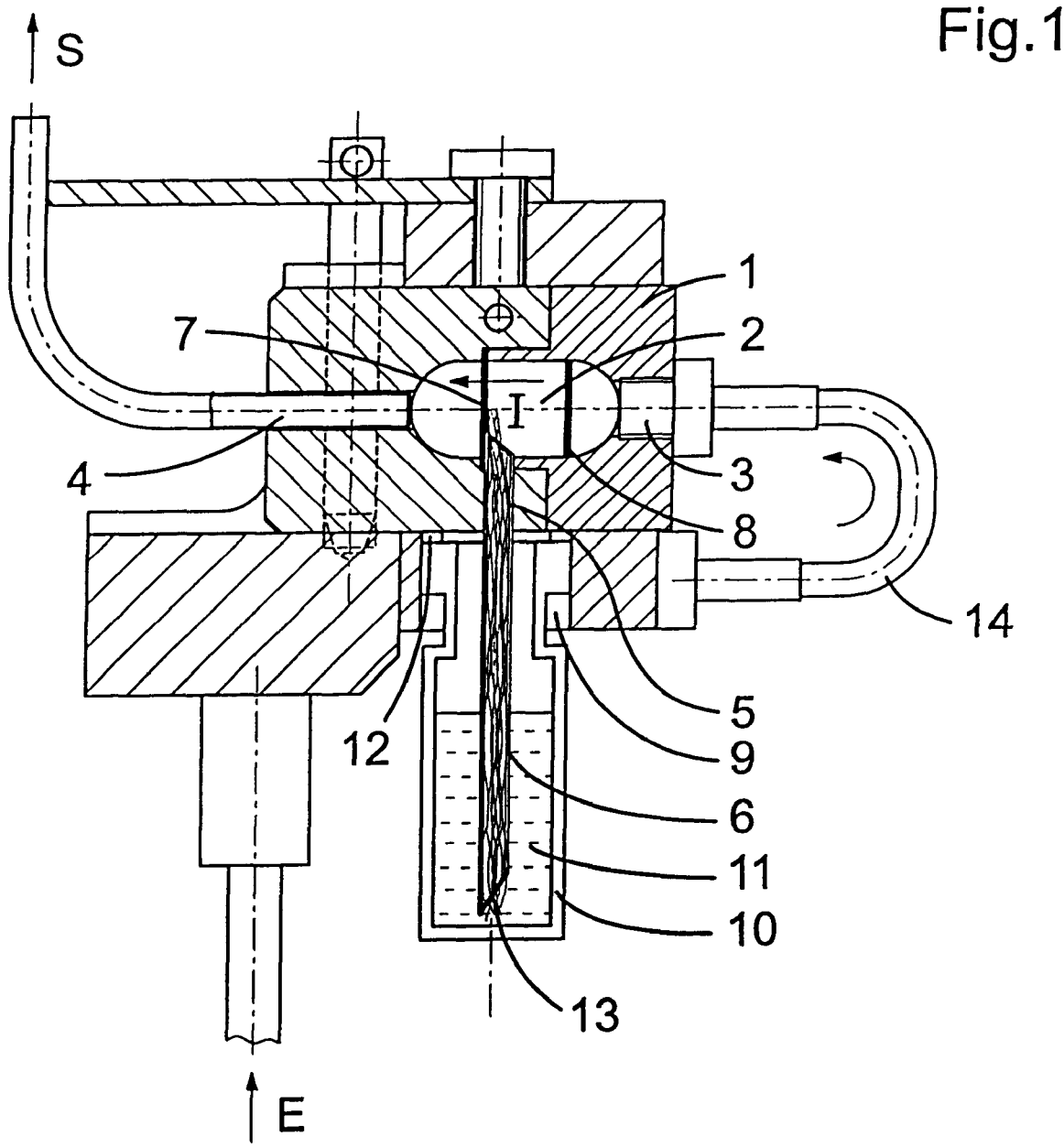
FIG. 1 is a section view of an embodiment of the device for diffusion according to the invention.

With reference first to FIG. 1, the device for diffusion according to the invention which is shown has a main body 1, generally realized in two parts fixed to each other and in a metal material, for example stainless steel, having an inner chamber 2 and passages 3, 4, respectively for the entry of air and for letting air out, opening horizontally into the chamber 2. A passage 5 directed downwards and opening into the lower side of body 1 is also formed starting from inner chamber 2. The main body 1, as well as the other forming parties, can also be made of a material other than metal, for example of a synthetic material, which is either machine made or molded, and inert to the products one wants to diffuse and to the possible solvents containing the products.

Moreover, a capillary element is arranged in the passage 5 directed downwards and cooperates with it, the capillary element being made for example of a hollow needle 6. The upper end of this hollow needle 6 is in contact with a diffusion grid or screen 7 arranged in the inner chamber 2 perpendicularly to the flow of air (arrow I). As the case may be, a second screen to cut the flow 8 can be disposed in the inner chamber 2, also perpendicularly to the air flow (I), but above the diffusion grid 7.

On the other hand, the body 1 of the diffusion device presents in its lower part and in relation with the passage 5 directed downwards a lodging 9 intended to receive, in the operating position, the upper end of a bottle 10 which serves as a reservoir for the aromatic liquid 11 to be tested. Preferably, this bottle 10 is sealed for example with a diaphragm of the septum type 12, the latter being intended to be pierced, when the bottle 10 is installed in lodging 9, by the free lower end of the hollow needle 6. In practice, the bottle 10 is maintained in the operating position shown by the simple rubbing of needle 6 with the elastic material of septum 12.

In principle, the hollow needle 6 could be used on its own to carry out the role of capillary element to bring the aromatic liquid 11 from the bottle 10 to the diffusion screen 7, provided its diameter is appropriate therefore. On the contrary, in practice and preferably, a wick 13 is arranged inside needle 6, and consequently inside passage 5, needle 6 then serving as a means to guide and protect wick 13 which fulfills the role of capillary element. This wick 13 is thus in contact, on the one hand, through its lower extremity, with the liquid 11 to be diffused and, on the other hand, through its upper extremity, with the diffusion grid 7, on which it can be fixed for example by means of just a gluing point.

Preferably, the wick 13 is made of a material which is inert to the product to be diffused, such that, even if this wick 13 is only a vector for the product for a relatively short time, it does not risk modifying the chemical characteristics and in particular the odor characteristics of the product. Appropriate materials for the wick 13 include for instance cotton, cellulose fibers, glass fibers or rock fibers, etc., cotton being preferred. Moreover, this wick 13 may also comprise only a very limited number of forming filaments (for instance 2 to 5).

As for the diffusion grid 7 itself, it can be advantageously formed of a stainless steel cloth having mesh width of 0.15 to 0.4 mm and be formed of wires of around 0.1 to 0.2 mm diameter. More particularly, cloth having a mesh width of 0.20, 0.22, 0.25, 0.32 mm, formed respectively of wires of 0.125, 0.16, 0.18, 0.18 mm diameter, can be used. Depending on the variant, the diffusion grid 7 may also be made of a synthetic material, for example Teflon®.

As far as the operation of the diffusion device described above with reference to FIG. 1 is concerned, it consists in introducing a flow of air under pressure in the circuit through entry E, this air circuit passing by an external circuit 14, then horizontally following arrow 1 inside the inner chamber 2 via passage 3. It is in this chamber 2 that the air flow is put into contact with the liquid to be diffused, which has been brought to the diffusion grid 7 by capillarity. The air flow can then carry the volatile emanation (headspace) with it, exiting chamber 2 via passage 4, and being then directed to the exit passage 5, where the user can then smell the odor of the vapor phase emanating from the aromatic liquid to be tested, the air flow being totally devoid of any liquid micro-drop, this being rendered possible by appropriately adjusting the pressure of the air passing through the diffuser.

Figure 2:
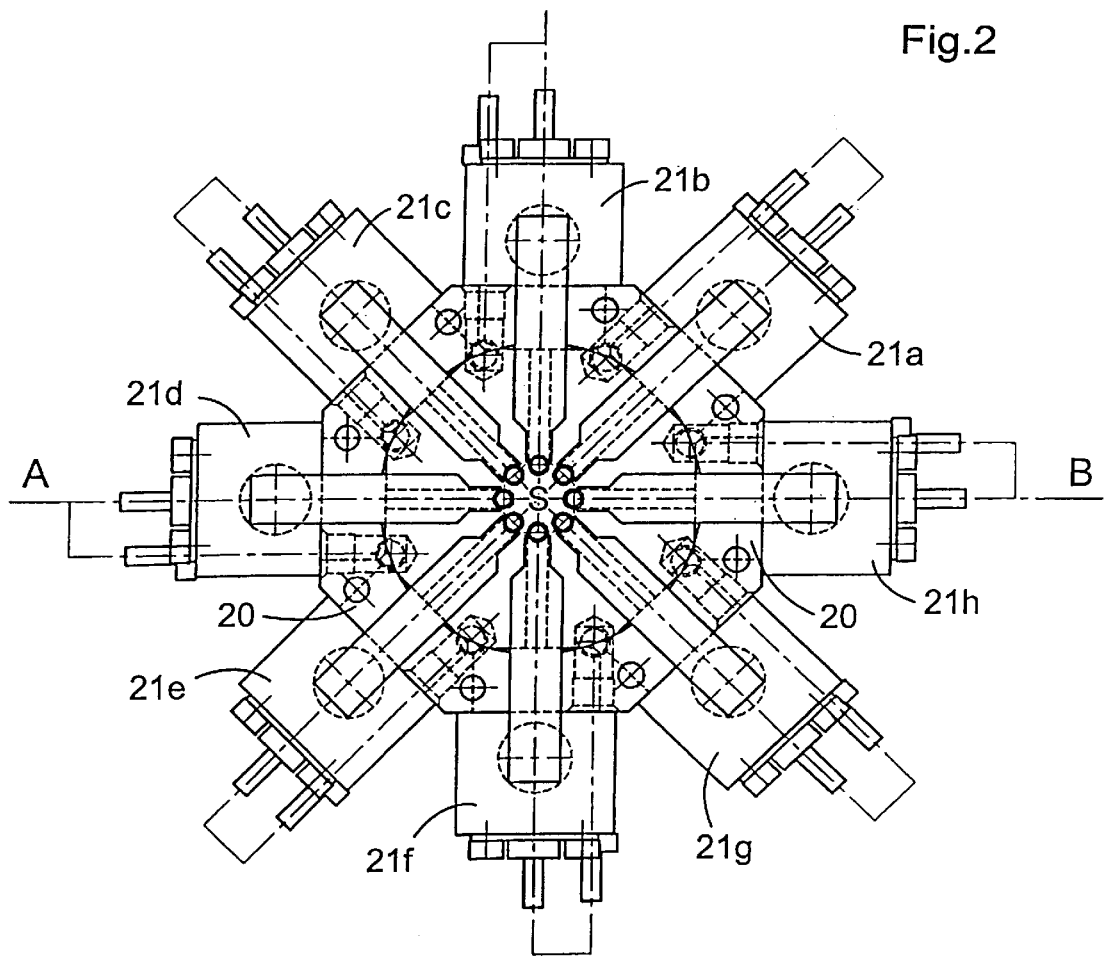
FIG. 2 is a plane view of an embodiment of the apparatus for the olfactive evaluation of scents according to the invention.

According to another object of the invention, several diffusion devices, such as that described above, can be radially disposed in the form of a star to form an apparatus intended for the odor evaluation of several scents, either separately or in the form of mixtures of several such scents. According to the embodiment illustrated by way of example in FIG. 2, the apparatus has a main frame or body 20 which is circular or polygonal, as represented octagonal. On each of the eight sides of this main frame 20 there is mounted a diffusion device 21a to 21h, for example of the type of that described with reference to FIG. 1.

Of course, each diffusion device 21a–21h is connected to separate operating controls which make it possible to activate each of them either separately, one by one, or simultaneously to one or more of the other devices. Preferably, the controls of the diffusers are brought together into a same panel, and the source of pressurized air is common to all the devices.

Each one of these eight devices 21a to 21h presents a passage 5 directed upwards and arranged in the center of the main frame 20 of the apparatus, the distance to be covered by the air flow charged with scent headspace being the same for all the diffusors, Moreover, the arrangement of the eight passages 5 in the center of the frame 20 makes it possible for the user to activate several of the diffusors 21a–21h to obtain and evaluate the odor of a mixture of emanations without having to move himself.

Figure 3:
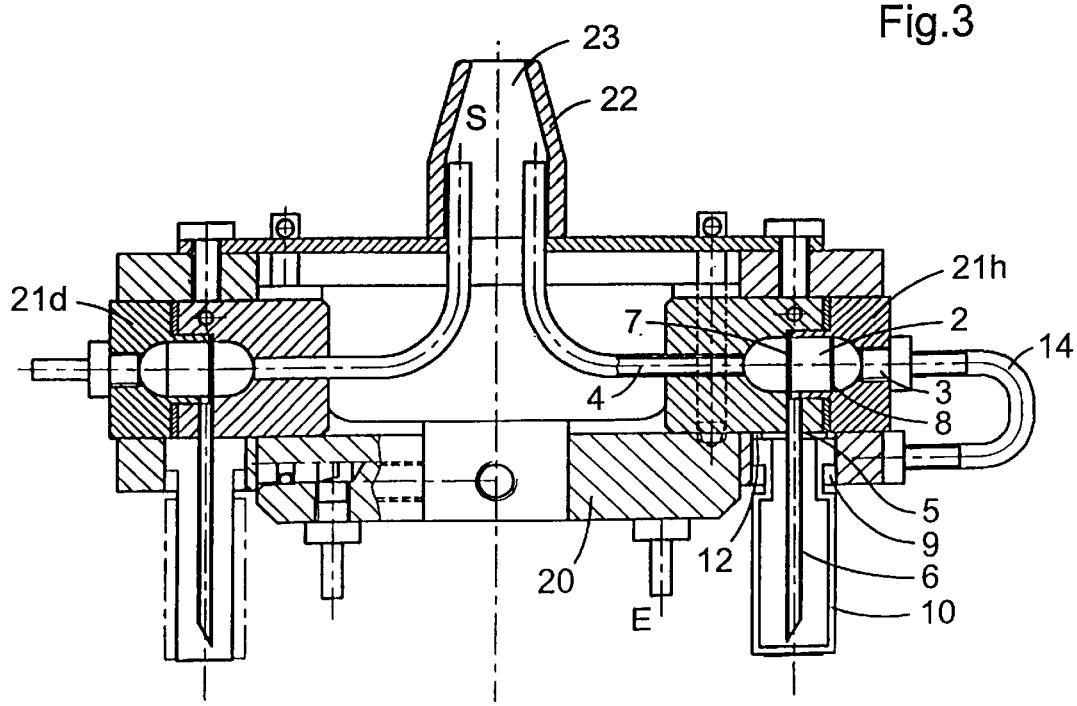
FIG. 3 is a section view following line A-B of FIG. 2.

The section represented in FIG. 3 shows two diffusion devices diametrically opposed, the reference figures indicated on one of the devices corresponding to those of FIG. 1. Moreover, this FIG. 3 represents an embodiment of the invention in which a cover 22 is placed above the outlets S of the eight diffusion devices 21a to 21h forming the apparatus illustrated in FIG. 2. This cover 22 presents a central opening 23 and thus improves the use conditions of the apparatus.

Therefore, thanks to the present invention, the user, whether he is a professional or not, is provided with an apparatus for the olfactive evaluation of a pure perfuming ingredient or of a mixture of perfumes which is polyvalent, easy to use and can be easily carried (portable) as a result of its small size and compact nature. When compared to the known diffusers, the diffusion device, and the apparatus according to the invention which carries several of the devices, present the following advantages:

the aromatic liquid is stored in a closed bottle which allows a constant diffusion in time of the liquid and a longer operating period;

replacement of the bottles is easy, which is an advantage both for cleaning up the apparatus as for its polyvalence;

the absence of liquid micro-drops (spray) in the air flow to be smelt by the user;

a reduced or totally eliminated risk of modification of the odor characteristics as a result of the absence of a solid absorption carrier for the aromatic liquids;

the many possibilities of use for the professionals and for the public at large, namely thanks to the radial conception in a star form of the diffusers on the main body of the apparatus.

What is claimed is:

1. A device for diffusing aromas which comprises a bottle having a bottom and defining an interior that contains therein a liquid aromatic product that includes an aroma to be diffused; a device body for diffusing the aroma from the liquid aromatic product, the body being removably mounted on the bottle and having an inner chamber which communicates with the bottle interior when in an operating position;

entrance and exit passages for movement of air, the passages being connected to a pressurized air circuit that opens into the inner chamber and cause movement of air along a path from the entrance to exit passages; a diffusion screen arranged in the inner chamber and positioned in the moving air path between the entrance and exit passages in a position that is perpendicular to the air movement path so that it can carry the aroma without also carrying microdrops of the liquid aromatic product, and a capillary element extending from the liquid aromatic product to the diffusion screen for directing the liquid aromatic product to the diffusion screen under capillary action, wherein the screen exposes the liquid aromatic product to the moving air which carries the aroma out of the device.

2. The device of claim 1, wherein the capillary element is a hollow needle having one end that cooperates with the diffusion grid and another end disposed inside the bottle interior.

3. The device of claim 2, which further comprises a wick arranged inside the hollow needle, wherein one end of the wick is in contact with the diffusion screen and another end positioned close to the bottom of the bottle.

4. The device of claim 1, which further comprises a cut-flow grid arranged in the inner chamber adjacent the diffusion screen.

5. The device of claim 1, which further comprises operating means for adjusting pressurized air flow and air movement through the entrance and exit passages.

6. An apparatus for dispensing and evaluating aroma odors, comprising a plurality of devices for diffusing aromas; and a main frame having a central portion around which the plurality of devices are mounted, each of the devices comprising a bottle having a bottom and defining an interior that contains therein a liquid aromatic product that includes an aroma to be diffused; a device body for diffusing the aroma from the liquid aromatic product, the body being removably mounted on the bottle and having an inner chamber which communicates with the bottle interior when in an operating position; entrance and exit passages for movement of air, the passages being connected to a pressurized air circuit that opens into the inner chamber and cause movement of air along a path from the entrance to exit passages; a diffusion screen arranged in the inner chamber and positioned in the moving air path, and a capillary element extending from the liquid aromatic product to the diffusion screen for directing the liquid aromatic product to the diffusion screen under capillary action, wherein the screen exposes the liquid aromatic product to the moving air which carries the aroma out of the device and wherein the exit passages of the devices are located in the central part of the frame.

7. The apparatus of claim 6 wherein the frame is circular and each exit passage is arranged to direct aroma containing air toward the central portion of the frame.

8. The apparatus of claim 6 wherein the frame is polygonal with each face including an exit passage arranged to direct aroma containing air toward the central portion of the frame.

9. The apparatus of claim 8, wherein that the frame is octagonal.

10. The apparatus of claim 6, which further comprises a cover having a central aperture directed upwards and covering the exit passages.

11. The apparatus of claim 6, which further comprises operating means for adjusting pressurized air flow and air movement through the entrance and exit passages of each of the devices.

12. The apparatus of claim 11, wherein the means for operating the devices is assembled on a same panel and with a common source of pressurized air for all the devices.

13. The apparatus of claim 12, arranged such that each device can be operated individually.

14. The apparatus of claim 12, arranged such that multiple devices can be operated simultaneously.

15. The apparatus of claim 6, wherein the diffusion screen in each device is located between the entrance and exit passages in a position that is perpendicular to the air movement path so that it can carry the aroma without also carrying microdrops of the liquid aromatic product.

* * * * *